United States Patent
Pizzi et al.

(10) Patent No.: US 8,126,543 B2
(45) Date of Patent: Feb. 28, 2012

(54) DEVICE FOR ELECTROCHEMOTHERAPY

(75) Inventors: Marco Pizzi, Turin (IT); Valentina Grasso, Carignano (IT)

(73) Assignee: C.R.F. Società Consortile per Azioni, Orbssano (Torino) (IT)

( * ) Notice: Subject to any disclaimer, the term of this patent is extended or adjusted under 35 U.S.C. 154(b) by 1395 days.

(21) Appl. No.: 11/070,319

(22) Filed: Mar. 1, 2005

(65) Prior Publication Data

US 2005/0245857 A1 Nov. 3, 2005

(30) Foreign Application Priority Data

May 3, 2004 (EP) .................................... 04425310

(51) Int. Cl.
*A61N 1/00* (2006.01)
(52) U.S. Cl. ......................................................... 604/20
(58) Field of Classification Search .................. 607/2, 3, 607/33, 50, 61, 72, 88, 96, 98, 99, 101, 103–105, 607/113, 116, 120, 154; 606/27; 600/9, 600/10, 12; 604/20, 21, 891.1; 31/2, 3, 33, 31/50, 61, 72, 88, 96, 98, 99, 101, 103–105, 31/113, 116, 120, 154
See application file for complete search history.

(56) References Cited

U.S. PATENT DOCUMENTS

| | | | | | |
|---|---|---|---|---|---|
| 4,330,593 | A | * | 5/1982 | Shrout et al. | 428/407 |
| 5,620,740 | A | * | 4/1997 | Baliga et al. | 427/100 |
| 5,928,224 | A | * | 7/1999 | Laufer | 606/27 |
| 6,021,347 | A |   | 2/2000 | Herbst et al. | 607/2 |
| 6,206,914 | B1 | * | 3/2001 | Soykan et al. | 623/1.42 |
| 6,366,808 | B1 | * | 4/2002 | Schroeppel et al. | 607/2 |
| 6,431,175 | B1 | * | 8/2002 | Penner et al. | 128/899 |
| 6,622,049 | B2 | * | 9/2003 | Penner et al. | 607/59 |
| 2002/0077676 | A1 |   | 6/2002 | Schroeppel et al. | 607/75 |
| 2002/0111601 | A1 | * | 8/2002 | Thompson | 604/514 |
| 2002/0188323 | A1 | * | 12/2002 | Penner et al. | 607/2 |
| 2004/0010290 | A1 |   | 1/2004 | Schrooeppel et al. | 607/3 |
| 2005/0251234 | A1 | * | 11/2005 | Kanzius et al. | 607/101 |

FOREIGN PATENT DOCUMENTS

DE 4201461 A1 7/1993
EP 0543498 A1 10/1992

OTHER PUBLICATIONS

Xi, Jianzhong; Dy, Eric; Hung, Ming-Tsung; Montemagno, Carlo; Development of a self-assembled muscle-powered piezoelectric microgenerator; 2004 NSTI Nanotechnology Conference and Trade Show—NSTI Nanotech 2004, Conference No. 63724, Publication Date Nov. 5, 2004.*
European International Search Report dated Oct. 29, 2004.

* cited by examiner

*Primary Examiner* — Niketa Patel
*Assistant Examiner* — Michael D Abreu
(74) *Attorney, Agent, or Firm* — Young Basile

(57) ABSTRACT

A device for electrochemotherapy comprises an electric micro- or nano-capacitor which can be injected in the blood circulation of a human or animal body, including a pyroelectric or piezoelectric layer which can be excited from the outside of the human or animal body, for generating an electric field in the immediate vicinity of a tumor cell, together with the administration of a chemotherapeutic agent. The chemotherapeutic agent may be administered with independent means, but preferably is bound to the outer surface of the microcapacitor and is delivered because of the temperature increase which is generated at the time of the microcapacitor excitation.

8 Claims, 2 Drawing Sheets

DEVICE FOR ELECTROCHEMOTHERAPY

BACKGROUND OF THE INVENTION

The present invention relates to an intravascular device which can be injected within the blood circulation of a human or animal body, for electrochemotherapy applications.

The electrochemotherapy has developed in recent years (see, for example, US2004/0010290 A1, US2002/077676 A1) and consists in the combined treatment of tumor cells by a chemotherapeutic agent and pulsed electric fields. Such a strategy may increase the effectiveness of the pharmaceutical product up to hundreds or a thousand times and it has caused a high percentage of successes in clinical tests. The devices for electrochemotherapy used so far, however, only allow the treatment of readily accessible tumors (mainly melanomas) or involve the use of highly invasive means, such as catheters or endoscopes.

SUMMARY OF THE INVENTION

The aim of the present invention is to carry out a device for electrochemotherapy which is able to overcome these drawbacks.

In view of attaining this aim, the object of the invention is a device for electrochemotherapy, comprising at least an electric microcapacitor, with a maximum dimension not above 10 μm, and preferably lower than 1 μm which can be injected in the blood circulation of a human or animal body, including two layers acting as electrodes between which a ferroelectric layer is interposed, and means for generating an electric potential at the electrodes of said microcapacitor from the outside of the human or animal body.

In a first embodiment, the ferroelectric layer of the microcapacitor is of a pyroeletric type, and the aforesaid means for generating the electric potential include a source of alternating electric field suitable for causing, from the outside of the human or animal body, a temperature increase of the aforesaid pyroelectric layer, with a consequent generation of an electric potential at the microcapacitor electrodes.

In a second embodiment, the aforesaid ferroelectric layer of the microcapacitor is of a piezoelectric type, and the aforesaid means include a vibration source, suitable for causing, from the outside of the human or animal body, a vibration of the piezoelectric layer, with a consequent generation of an electric potential at the microcapacitor electrodes.

It can be forecast to administer the chemotherapeutic agent with means independent from the device according to the invention. However, preferably, the microcapacitor according to the invention has an outer surface to which a medicinal substance, releasable after a temperature increase, is bound. The microcapacitor surface may then be functionalized for the purpose of a local administration of the medicinal agent. As already shown, the application, for example, of an alternating electromagnetic field from the outside of the human or animal body, produces a temperature increase and an electric potential at the microcapacitor electrodes. In this way, both the electrochemotherapeutic effect and also the combination thereof with a hyperthermia treatment is obtained.

BRIEF DESCRIPTION OF THE DRAWINGS

Further features and advantages of the invention will result from the following description, with reference to the enclosed drawings, wherein.

DETAILED DESCRIPTION OF THE INVENTION

Figure 1:
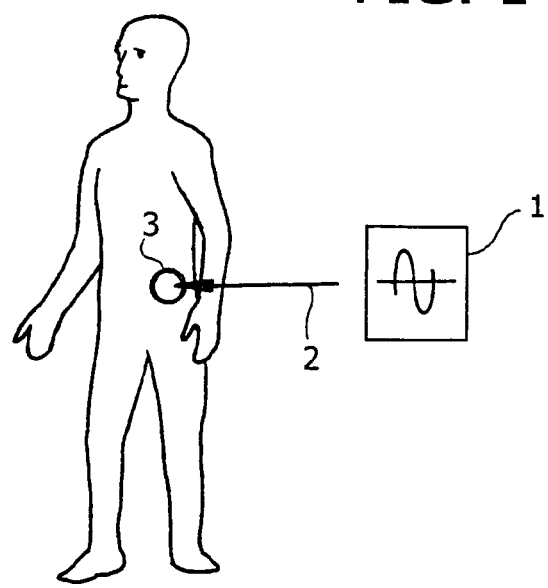
FIG. 1 diagrammatically shows the use of the device according to the invention.

In FIG. 1, the numeral 1 generally shows a source of an alternating electromagnetic field, by which an electromagnetic radiation is sent in the direction of a human body area where, for example, a tumor is located.

Figure 2:
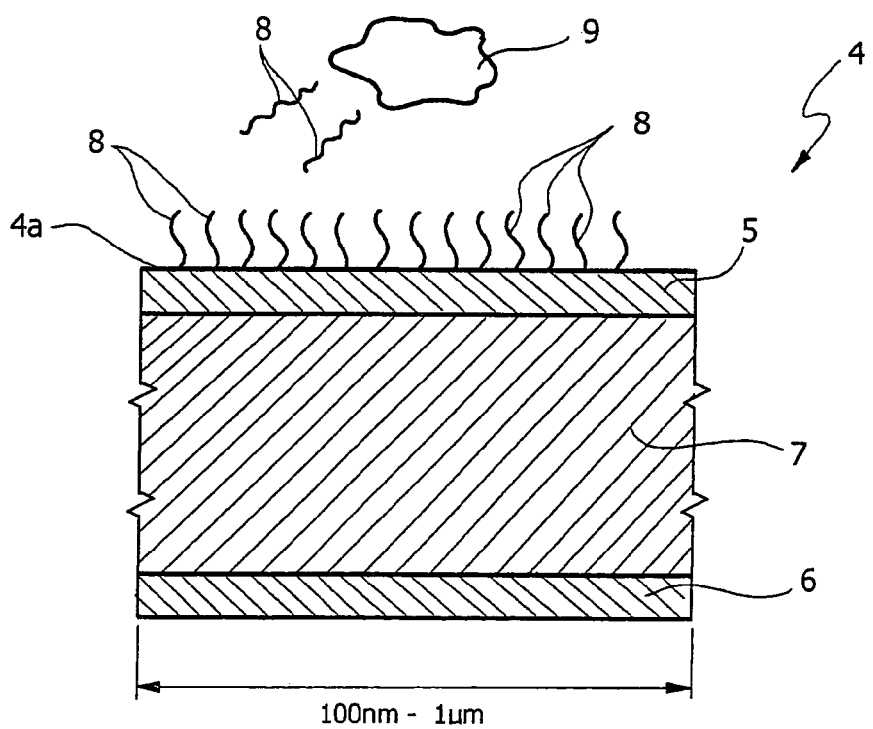
FIG. 2 shows a sectional and scale-enlarged electric microcapacitor according to the invention.

In FIG. 2, numeral 4 generally shows an electric micro- or nano-capacitor which can be injected in the blood circulation of a human or animal body. The maximum outer dimension of such microcapacitor is preferably between 100 μm and 1 μm, and generally is then lower than 10 μm. The microcapacitor 4 includes two electrodes 5, 6 between which a ferroelectic layer 7 is interposed, for example of a pyroelectric type or piezoelectric type. In the first case, the application of the electromagnetic radiation 2 produces a temperature increase of the pyroelectric layer 7, with a consequent generation of an electric potential at the electrodes 5, 6. In contrast, in case of using a piezoelectric layer, instead of the source 1 of an electromagnetic radiation, a vibration source is used, for the purpose of producing a vibration of the piezoelectric layer 7 which produces the electric potential required for the electrodes 4, 6.

Preferably, at least part of the outer surface of the microcapacitor 4 is "functionalized", that is arranged for bounding a chemotherapeutic agent 8 thereof. The bonds between the agent 8 and the surface 4a are broken because of the temperature increase caused by the outside, in such a way that the active substance may directly and selectively attack the tumor cell 8 (FIG. 2), at the same time of the localized application of the electric field always produced by the microcapacitor 4.

Figure 3:
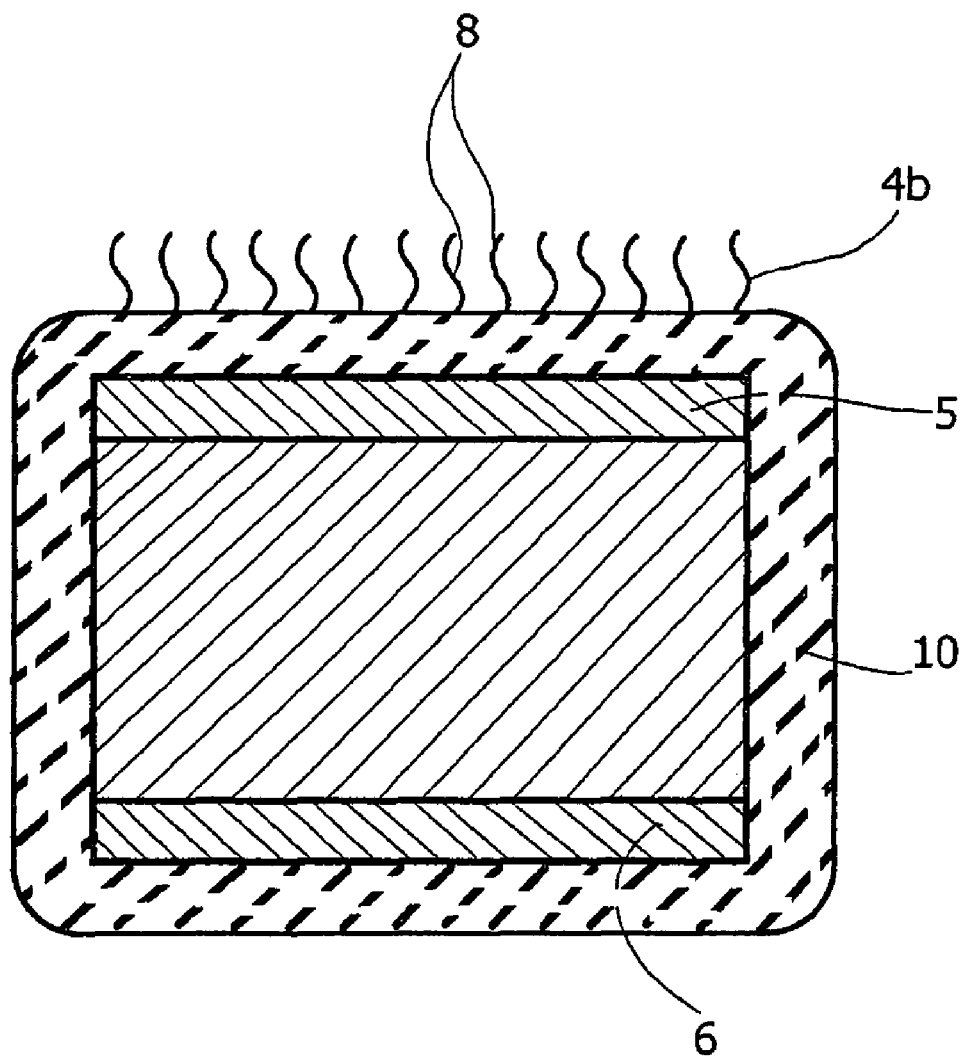
FIG. 3 shows a variation of FIG. 2.

FIG. 3 shows a variation wherein the whole microcapacitor is coated with an insulating layer 10 and wherein at least a part of the outer surface is arranged with an adhesive-promoter layer 4b, for its functionalization with the active substance 8.

As pyroelectric or piezoelectric materials for the layer 7 of the microcapacitor, for example, ceramic materials and ferroelectric polymers, such as biocompatible PVDF, can be used. The manufacturing is preferably carried out by a multilayer deposition technique, followed by photolithography and "etching". The first layer deposited on a substrate is a sacrificial layer, to which an electrode follows, then the ferroelectric layer (with high pyroelectric or piezoelectric properties) and a second electrode. The electrodes are necessary for the material polarization, but in the final nano-capacitor they could also be avoided, if a piezoelectric material, which can be excited by an outer vibration source, is used. If the excitation is of an electromagnetic type, it is however required at least a metal layer which works as a micro-antenna. The presence of a metal electrode can also help its functionalization.

The control parameters (excitation means, frequency, number of pulses, pulses length) may change for the purpose of determining the optimal conditions for an efficacious electrochemotherapy.

Of course, without prejudice for the principle of the invention, construction details and embodiments could widely vary with respect to what has been described by mere way of example, without leaving for this reason the ambit of the present invention.

The invention claimed is:

1. Device for electrochemotherapy, comprising:
   an intravascular, electric microcapacitor configured for injection with an injector in the blood circulation of a human or animal body such that the microcapacitor is decoupled from the injector after injection, wherein the microcapacitor has a maximum dimension not above 10 μm and includes two layers acting as electrodes, between which a ferroelectric layer is interposed; and means for stimulating the ferroelectric layer to generate an electric potential at the electrodes of said microcapacitor from the outside of the human or animal body.

2. Device according to claim 1, wherein the ferroelectric layer is a pyroelectric material, and the aforesaid means include a source of alternating electromagnetic field suitable for causing, from the outside of the human or animal body, a temperature increase of the pyroelectric material constituting the aforesaid layer, with a consequent generation of an electric potential at the electrodes of the microcapacitor.

3. Device according to claim 1, wherein the ferroelectric layer is of a piezoelectric type, and in that said means include a source of vibration suitable for causing, from the outside of the human or animal body, a vibration of the piezoelectric material constituting the aforesaid layer, with a consequent generation of an electric potential at the electrodes of said microcapacitor.

4. Device according to claim 1 further comprising a medicinal substance bound to at least part of an outer surface of the microcapacitor and configured to be releasable from the microcapacitor upon generation of the electric potential.

5. Device according to claim 1, wherein the microcapacitor further comprises an insulating coating on a surface of the microcapacitor.

6. Device according to claim 1, wherein said microcapacitor further comprises a metal layer acting as a micro-antenna.

7. Device according to claim 1 further comprising a medicinal substance bound to at least a part of an outside surface of the microcapacitor and configured to be releasable after a temperature increase.

8. Device according to claim 1, wherein the maximum dimension of the microcapacitor is 1 μM.

* * * * *